US008067043B2

(12) United States Patent
Managoli

(10) Patent No.: US 8,067,043 B2
(45) Date of Patent: Nov. 29, 2011

(54) HERBAL COMPOSITION FOR TREATMENT OF HYPERLIPIDEMIA AND THE INHIBITION OF MYOCARDIAL INFARCTION

(75) Inventor: Nandkishor Bapurao Managoli, Surat (IN)

(73) Assignee: Sahajanand Biotech Pvt. Ltd., Surat (IN)

( * ) Notice: Subject to any disclaimer, the term of this patent is extended or adjusted under 35 U.S.C. 154(b) by 389 days.

(21) Appl. No.: 12/188,566

(22) Filed: Aug. 8, 2008

(65) Prior Publication Data

US 2009/0263466 A1    Oct. 22, 2009

(30) Foreign Application Priority Data

Apr. 17, 2008  (IN) .......................... 1001/DEL/2008

(51) Int. Cl.
*A61K 36/48* (2006.01)
*A61K 36/00* (2006.01)
*A61K 36/82* (2006.01)
*A61K 9/00* (2006.01)
*A61K 47/00* (2006.01)

(52) U.S. Cl. ........ 424/757; 424/725; 424/729; 424/400; 424/439

(58) Field of Classification Search .................. None
See application file for complete search history.

(56) References Cited

FOREIGN PATENT DOCUMENTS

| CN | 101045077 A | * | 10/2007 |
| IN | 200600172 I2 | * | 5/2008 |

OTHER PUBLICATIONS

Rose et al. "Herbal Support for a Health Cardiovascular System". Clinical Nutrition Insights, vol. 6, No. 16 (1999) pp. 1-6.*
Ram, A. "Effect of plumbago zeylanica in hyperlipidaemic rabbits and its modification by vitamin E." Indian Journal of Pharmacology, vol. 28, No. 3 (Sep. 1996) pp. 161-6, Abstract.*
Agrawal. "Medicinal Properties of Neem: New Findings". Internet Archive Date: Jan. 22, 2003 [Retrieved from the Internet on: Mar. 12, 2010]. Retrieved from: <URL: http://web.archive.org/web/20030122180243/http://www.infinityfoundation.com/mandala/t_es/t_es_agraw_neem.htm>.*
Lo et al. "Soy fiber improves lipid and carbohydrate metabolism in primary hyperlipidemic subjects." Atherosclerosis. vol. 62, Issue 3 (Dec. 1986) pp. 239-248, Abstract.*
(U1) Yang et al. Green, oolong and black tea extracts modulate lipid metabolism in hyperlipidemia rats fed high-sucrose diet. J Nutr Biochem. Jan. 2001;12(1):14-20.*
Bossaller et al., "Impaired Muscarinic Endothelium-dependent Relaxation and Cyclic Guanosine 5' Monophosphate Formation in Atherosclerotic Human Coronary Artery and Rabbit Aorta," J. Clin. Invest., Jan. 1987, 79:170-171.
Ibengwe et al., "Changes in mechanical responses of vascular smooth muscles to acetylcholine, noradrenaline and high potassium solution in hypercholesterolaemic rabbits," Br. J. Pharmacol., 1986, 87:395-402.
Sharma et al., "Effect of Fenugreek Seeds on Blood Glucose and Serum Lipids in Type I Diabetes," Eur. J. Clin. Nutr., 1990, 44:301-6.
Sharma et al., "Hypolipidemic and Antiatherosclerotic Effects of Plumbagin in Rabbits," Indian J. Physiol. Pharmacol., 1991, 35(1):10-4.
Kohno et al., "Decreases in Serum Triacyglycerol and Visceral Fat Mediated by Dietary Soybean B-conglycinin," Journal of Atherosclerosis and Thrombosis, 2006, 13(5):247-55.
Jaiswal et al., "Anxiolytic Activity of Azadirachta Indica Leaf Extract in Rats," Indian J. Exp. Biol., Jul. 1994, 32:489-91.
Dwivedi et al., "Beneficial Effects of *Terminalia arjuna* in Coronary Artery Disease," Indian Heart J., Sep.-Oct. 1997, 49(5): 507-10.
Folkers et al., "Lovastatin Decreases Coenzyme Q levels in Gumans," Proc. Natl. Acad. Sci. USA, Nov. 1990, 87:8931-41.
Mitka, M., "Biomarkers for Coronary Heart Disease: Predictive Value or Background Noise?", JAMA , Dec. 2004, 292 (23):2824-2825.
Ridker et al., "C-Reactive Protein Levels and Outcomes After Statin Therapy," New Eng. J. Med., Jan. 2005, 352:20-8.
Nissen et al., "Statin Therapy, LDL Cholesterol, C-Reactive Protein, and Coronary Artery Disease." New Eng. J. Med., Jan. 2005, 352:29-38.
Thompson Coon et al., "Herbs for Serum Cholesterol Reduction: A Systematic Review," J. Fam. Practice, Jun. 2003, 52(6)1-16.
Szapary et al., "A double Blind, Randomized, Placebo Controlled Clinical Trial of Standardized Guggul Extract in Patients with Hypercholesterolemia," JAMA, Aug. 2003, 290(6)765-772.
Kuppurajan et al., "Effect of Guggulu (Commiphora Mukul-Engl.) on Serum, Lipids in Obese, Hypercholesterolemic and Hyperlipemic Cases," J. Assoc. Phys. India, May 1978, 26:367-73.
Cholidhary et al., "Modulation of Glycoxalase, Glutathione S-Transferase and Antioxidant Enzymes in the Liver, Spleen and Erythrocytes of Mice by Dietary Administration of Fenugreek Seeds," Food and Chem. Toxicol., 2001, 39:989-997.
Stark et al., "The Effect of an Ethanol Extract Derived from Fenugreek (Trigonella Foenum-Graecum) on Bile Acid Absorption and Cholesterol Levels in Rats," Br. J. Nutr., 1993, 69:277-287.
Njoku et al., "Effect of *Azadirachta indica* Extract on Plasma Lipid Levels in Human Malaria," Boll. Chim. Farmac., Sep.-Oct. 2001, 140(5):367-70.
Costa et al., "Soy protein in the management of hyperlipidemia," The Annals of Pharmacotherapy, Jul.-Aug. 2000, 34(7-8):931-5.
Tikkanen et al., "Dietary Soy-Derived Isoflavone Phytoestrogens Could They Have a Role in Coronoary Heart Disease Prevention?", Biochem. Pharmacol., 2000, 60(1):1-5.
Acuff et al., "The Lipid Lowering Effect of Plant Sterol Ester Capsules in Hypercholesterolemic Subjects," Lipids in Health & Disease, Apr. 2007, 6:11.

(Continued)

Primary Examiner — Amy L Clark

(74) Attorney, Agent, or Firm — Volpe and Koenig, P.C.

(57) ABSTRACT

A pharmaceutical or medicinal herbal composition and method of making the composition comprised of a mixture of the following herbal ingredients: *Glycine max, Plumbago zeylanica, Terminalia arjuna, Trigonella-foenum-graecum, Coleus forskohlii, Commiphora mukul, Camellia sinensis,* and *Azadirachta indica.*

4 Claims, 4 Drawing Sheets

OTHER PUBLICATIONS

Gramaud et al., "Effects of Non-Esterified Stanols in a Liquid Emulsion on Cholesterol Absorption and Synthesis in Hypercholesterolemic Men," Eur. J. Nutr., 2002, 41:54-60.

Mussner et al., "Effects of Phytosterol Ester-Enriched Margarine on Plasma Lipoproteins in Mild to Moderate Hypercholesterolemia are Related to Basal Cholesterol and Fat Intake," Metabolism, Feb. 2002, 51:189-94.

Peluso, M. R., "Flavanoids Attenuate Cardiovascular Disease, Inhibit Phosphodiesterase, and Modulate Lipid Homeostasis in Adipose Tissue and Liver," Exp. Biol. Med., 2006, 231(8):1287-99.

Subapriya et al., "Chemopreventive Effects of Ethanolic Extract of Neem Leaf Against MNNG-Induced Oxidative Stress," Pharmazie, 2003, 58(7):512-7.

Lambert et al., "Mechanisms of Cancer Prevention by Tea Constituents," J. Nutr., 2003, 133:3262S-3267S.

Yang et al., "Prevention of Carcinogenesis by Tea Polyphenols," Drug Metab. Rev., 2001, 33:237-53.

Coimbra et al., "The Effect of Green Tea in Oxidative Stress," Clin. Nutr., 2006, 25(5):790-6.

Sivakumar et al., "Protective Effect of Plumbago Zeylanica Against Cyclophosphamide-Induced Genotoxicity and Oxidative Stress in Swiss Albino Mice," Drug and Chem. Toxicol., Sep. 2006, 29(3):279-88.

Wang et al., "The Hypolipidemic Natural Product *Commiphora mukul* and its Component Guggulsterone Inhibit Oxidative Modification of LDL," Atherosclerosis, 2004, 172(2):239-46.

Kaviarasan, et al., "Polyphenol-Rich Extract of Fenugreek Seeds Protect Erythrocytes from Oxidative Damage," Plant Foods for Human Nutr., 2004, 59(4):43-7.

Gauthaman et al., "*Terminalia arjuna* (Roxb.) Protects Rabbit Heart Against Ischemic-Reperfusion Injury: Role of Antioxidant Enzymes and Heat Shock Protein," J. Ethnopharmacol., 2005, 96(3):403-9.

Sung et al., "The Effects of Green Tea Ingestion Over Four Weeks on Atherosclerotic Markers," Assoc. Clin. Biochem., 2005, 42(4):292-7.

Son et al., "Antiplatelet Effect of Green Tea Catechins: A Possible Mechanism Through Arachidonic Pathway," Prostaglandins, Leukotrienes and Essential Fatty Acids, 2004, 71(1):25-31.

Ram et al., "Hypocholesterolemic Effects of *Terminalia arjuna* Tree Bark," J. Ethnopharmacol., 1997, 55(3):165-9.

Dubey et al., "Pharmacological Studies on Coleonol, a Hypotensive Diterpene from Coleus Forskohlii," J. Ethnopharmacol., 1981, 3(1):1-13.

Parmar et al., "Cardio-Protective Role of *Terminalia arjuna* Bark Extract is Possibly Mediated Through Alterations in Thyroid Hormones," Pharmazie 2006, 61(9):793-5.

Mondal et al., "Effect of Fenugreek Seeds on the Fasting Blood Glucose Level in Streptozotocin Induced Diabetic Rats," Mymensingh Med. J., 2004, 13(2):161-4.

\* cited by examiner

HERBAL COMPOSITION FOR TREATMENT OF HYPERLIPIDEMIA AND THE INHIBITION OF MYOCARDIAL INFARCTION

FIELD OF INVENTION

This invention relates to a novel herbal formulation that has been found to be effective in lowering several serum lipid types in the body. The present invention relates particularly to an herbal composition comprising a mixture of extracts and their active ingredients that is effective for the treatment of hyperlipidemia or elevated serum lipids and cholesterol, and inhibiting the progression to myocardial infarction. Since hyperlipidemia leads to atherosclerosis and its associated diseases, such as strokes and claudication, the formulation of the present invention may be used for the prevention of various vascular diseases in patients predisposed to these diseases.

BACKGROUND

Hyperlipidemia is a condition of elevated blood lipids/fats including cholesterol, cholesterol esters, phospholipids, triglycerides or lipoproteins in the bloodstream. Elevated low density lipoprotein-cholesterol (LDL-C) and reduced high density lipoprotein-cholesterol (HDL-C) levels are well recognized coronary heart disease (CHD) risk factors. When low density lipoproteins (LDL) are oxidized, they promote inflammation and lead to plaque formation or atherosclerosis. Inflammation is associated with various chronic diseases. C-reactive protein (CRP), a marker for acute inflammation, is known to be associated with progression to myocardial infarction. Atherosclerosis can lead to coronary heart disease, stroke, claudication and associated morbidity and mortality. Elevated cholesterol levels lead to the formation of fatty streaks and calcified plaques, and abnormalities in vascular functioning in both animals and humans. Population studies have shown that lipid-lowering strategies can reduce the risk of developing atherosclerotic disease, particularly myocardial infarction. The risks for hyperlipidemia associated diseases can be due to various physiological and behavioral, genetic factors and gender differences. These include hyperlipidemia, aging, obesity, high-fat diet, sedentary lifestyle, diabetes, stress, and depression.

As the size of a plaque grows, it can block the flow of blood (occlusion) in an artery, which can lead to ballooning, thinning and rupture of the artery wall (aneurysm and rupture) or blood clot formation (thrombosis). Plaque formation can occur in any blood vessel in the body, although it is commonly seen in the arteries supplying blood to the heart, the brain, and the lower limbs. There has been a global increase in the incidence, morbidity, and mortality associated with cardiovascular diseases and strokes. Current treatments for hyperlipidemia include the use of highly purified synthetic compounds like statins, fibrates, nicotinic acid and resins. These drugs have associated adverse side effects including allergy, nausea, vomiting, heart burn, constipation, steatorrhea, myalgia, muscle weakness and liver damage resulting from an irreversible increase in hepatic aminotransferase. The most popular drug statins were shown not to be effective in patients over the age of 70 and particularly in women. Furthermore, these drugs typically act by altering only one or two of the various factors that cause hyperlipidemia.

There is a need for improved medications that are holistic in action whereby they target multiple causative factors without adverse side effects. It is an object of the present invention to provide such a preparation.

SUMMARY

The present invention is directed to a pharmaceutical or medicinal herbal composition comprised of *Glycine max, Plumbago zeylanica, Terminalia arjuna, Trigonella-foenum-graceum, Coleus forskohlii, Commiphora mukul, Camellia sinensis*, and *Azadirachta indica* or a mixture of the active ingredients that have been extracted from such herbs. The herbal compositions of the present invention are effective for the treatment of conditions involving atherosclerosis, stress and anxiety, for use in cardioprotection, cardio-toning, hyperlipidemia and its associated diseases such as myocardial infarction, stroke and claudication among others.

One aspect of the present invention is directed to a pharmaceutical or medicinal herbal composition comprised of: *Glycine max* in an amount of about 10-15% by weight of the composition; *Plumbago zeylanica* in an amount of about 10-15% by weight of the composition; *Terminalia arjuna* in an amount of about 10-15% by weight of the composition; *Trigonella-foenum-graceum* in an amount of about 10-15% by weight of the composition; *Coleus forskohlii* in an amount of about 10-15% by weight of the composition; *Commiphora mukul* in an amount of about 10-15% by weight of the composition; *Camellia sinensis* in an amount of about 10-15% by weight of the composition; and *Azadirachta indica* in an amount of about 5-7.5% by weight of the composition.

Another aspect of the present invention is directed to a method for preparing a pharmaceutical or medicinal herbal composition. The method includes the steps of: (1) providing the following herbal ingredients: *Glycine max, Plumbago zeylanica, Terminalia arjuna, Trigonella-foenum-graceum, Coleus forskohlii, Commiphora mukul, Camellia sinensis*, and *Azadirachta indica*; (2) grinding the herbal ingredients into a fine powder form; (3) purifying the herbal ingredients by solvent extraction; (4) mixing the herbal ingredients in the following amounts: *Glycine max* in an amount of 10-15% by weight of composition; *Plumbago zeylanica* in an amount of 10-15% by weight of composition; *Terminalia arjuna* in an amount of 10-15% by weight of composition; *Trigonella-foenum-graceum* in an amount of 10-15% by weight of composition; *Coleus forskohlii* in an amount of 10-15% by weight of composition; *Commiphora mukul* in an amount of 10-15% by weight of composition; *Camellia sinensis* in an amount of 10-15% by weight of composition; and *Azadirachta indica* in an amount of 5-7.5% by weight of composition; and (5) processing the mixture of herbal ingredients in an acceptable form of administration.

Another aspect of this invention is directed to a method of treating symptoms associated with hyperlipidemia or cardiac disease. The method includes the steps of: (1) providing the following herbal ingredients in the following amounts: *Glycine max* in an amount of 10-15% by weight of composition; *Plumbago zeylanica* in an amount of 10-15% by weight of composition; *Terminalia arjuna* in an amount of 10-15% by weight of composition; *Trigonella-foenum-graceum* in an amount of 10-15% by weight of composition; *Coleus forskohlii* in an amount of 10-15% by weight of composition; *Commiphora mukul* in an amount of 10-15% by weight of composition; *Camellia sinensis* in an amount of 10-15% by weight of composition; and *Azadirachta indica* in an amount of 5-7.5% by weight of composition; and (2) administering the composition in the form of at least one of the group consisting of a gelatin capsule, a vegetarian capsule, a tablet, a liquid, a syrup, a dairy beverage, and a snack bar.

DETAILED DESCRIPTION OF THE PREFERRED EMBODIMENTS

Figure 1A:
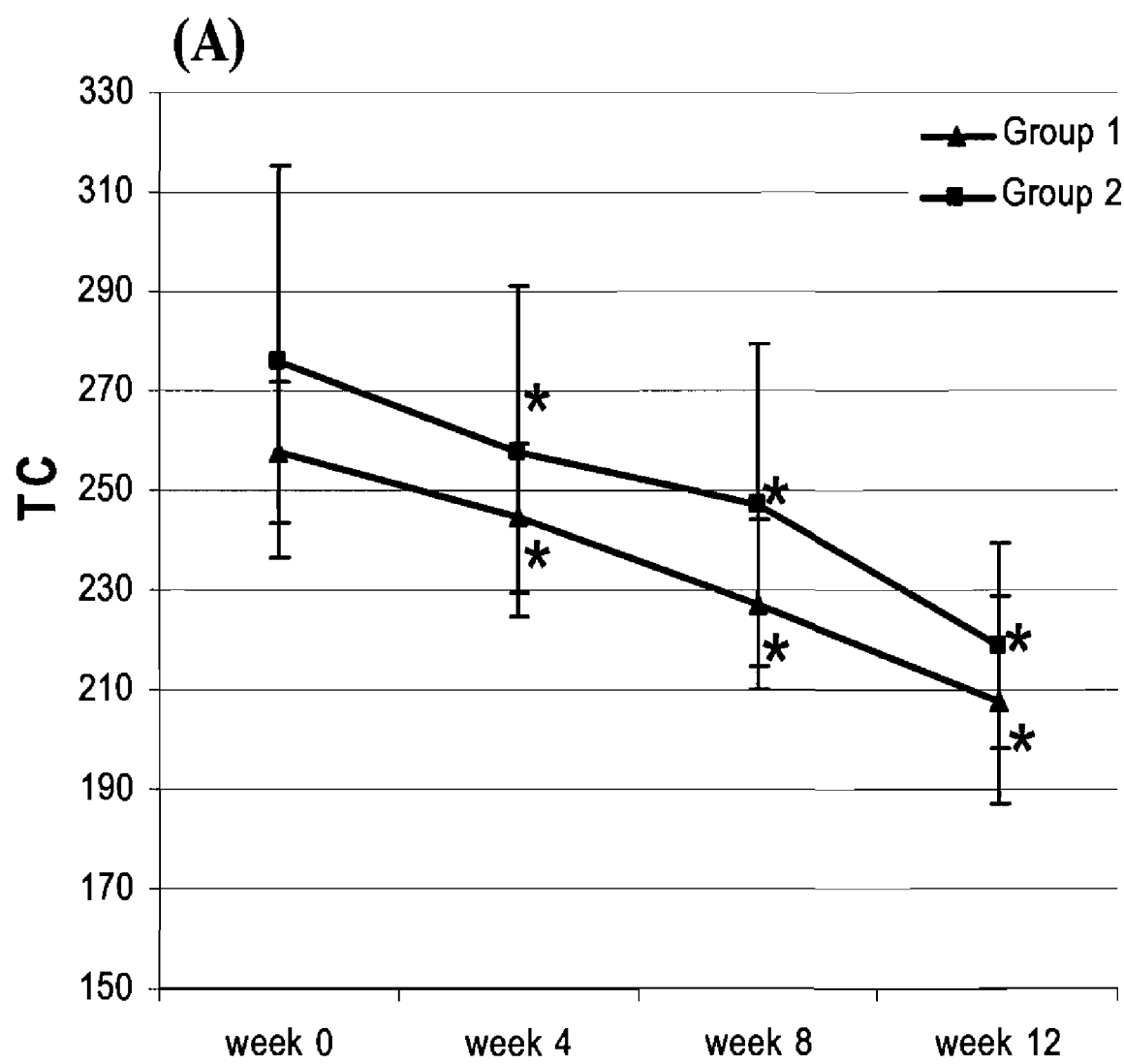
FIGS. 1(A) through 1(D) illustrate the results of human clinical trials following treatment with the herbal composition of the present invention. The subjects were divided into two (2) groups and the subjects' blood total cholesterol (TC) (FIG. 1(A)), total triglycerides (TG) (FIG. 1(B)), low density lipoprotein-cholesterol (LDL-C) (FIG. 1(C)) and very low density lipoprotein-cholesterol (VLDL-C) FIG. 1(D)) were measured during the course of a twelve (12) week treatment with the present herbal composition. Results are presented as Mean±SD, wherein a p-value less than 0.05 ($p<0.05$) is identified as (*) and a p-value greater than 0.05 ($p>0.05$) is identified as (**) and considered not significant, compared to baseline at week 0, using a paired t-test.

The following invention provides a pharmaceutical or medicinal composition that comprises the following mixture of herbal ingredients: *Glycine max, Plumbago zeylanica, Terminalia arjuna, Trigonella-foenum-graceum, Coleus forskohlii, Commiphora mukul, Camellia sinensis*, and *Azadirachta indica*, or a mixture of the active ingredients that have been extracted from such herbs, or chemically synthesized therefrom.

The preferred herbal ingredients and amounts used in the herbal compositions according to the present invention are set forth in Table 1. It should be understood that the proportions of the individual herbs may vary. In particular, the proportions of one or more of the components may vary in order to optimize the treatment effects to suit individual patients.

An important aspect of the herbal compositions of the present invention is that the composition contains a mixture of herbs, or extracts thereof, which provide more benefit than a single herb. An unexpected synergistic effect is exhibited by the combination of various ingredients in the present herbal compositions. The strategic combination of herbal ingredients of the present invention exhibits beneficial pharmacological effects when optimally combined. The active ingredients of the herbs are preferable combined in such a manner as to optimize and enhance the pharmacological effects with minimal or no adverse toxic reactions (which become a distinct possibility if the herbs are used singly at a concentration of 100%). An additional advantage of this poly herbal formula is that it minimizes the risk of developing drug resistance.

The herbal combinations described herein can be used as an alterative to conventional drugs or treatments and have been found to effectively treat or maintain a wide range of physiological and pathological conditions in the human body, especially in individuals with hyperlipidemia. For example, beneficial uses of the herbal compositions of the present invention include, without limitation:

(a) antilipemic (reduces high cholesterol/lipids, the building block for plaques);

(b) anti-atherosclerotic (prevents plaque formation);

(c) antioxidant (reduces lipid peroxidation, and is helpful because plaques are formed by oxidized LDL and other lipids);

(d) anti-inflammatory (reduces proteins that signal inflammation);

(e) anti-stress (reduces anxiety and stress, known causes of plaque build-up);

(f) cardiotonic (enables optimal heart function by acting on the cardiac smooth muscle); and (g) carioprotective (protects the heart from damage causing toxins).

The manufacture of an herbal composition and treatment with an herbal composition according to the present invention will now be illustrated by the following non-limiting examples. However, it will be appreciated by one of ordinary skills in the art that the proportions of ingredients, amounts of ingredients, and form of administration can vary without departing from the spirit of this invention.

TABLE 1

Preferred composition of herbal ingredients and their biomarkers.

| BOTANICAL NAME | STANDARDIZED COMMON NAME | PART USED | BIO MARKERS | PERCENT BY WEIGHT (%) OF THE COMPOSITION |
|---|---|---|---|---|
| *Glycine max* | Soy bean | Seed | about 40% isoflavone | 10-15 |
| *Plumbago zeylanica* | Ceylon leadwort | Root | about 0.08%-0.15% alkaloids | 10-15 |
| *Terminalia arjuna* | Arjuna | Bark | about 25% tannins and >1% arjunic acid | 10-15 |
| *Trigonella-foenum-graceum* | Fenugreek | Seed | about 10% saponins | 10-15 |
| *Coleus forskohlii* | Indian colchicum | Root | >2.5% forskolin and 10%-20% by HPLC | 10-15 |
| *Commiphora mukul* | Guggal | Resin | about 2.5%-10% guggal sterones by HPLC | 10-15 |
| *Camellia sinensis* | Tea | Leaf | >45% polyphenols by HPLC | 10-15 |
| *Azadirachta indica* | Neem | Bark | about 2.5% bitters | 5-7.5 |

Example

Method of Extraction and Manufacture

A polyherbal formulation was prepared in accordance with the present invention by harvesting and cleaning each of the raw herbal ingredients using standard protocols, grinding each ingredient to a fine powder form, diluting each ingredient, and subjecting each of the herbal ingredients to standard solvent extraction methods, including alcoholic and hydroalcoholic solvent extraction, chlorofluorocarbon gas extraction, carbon dioxide ($CO_2$) gas extraction, or any other suitable extraction method.

By way of illustration only, the extraction can be performed by using volatile chlorofluorocarbon gas. This process has the advantage of being fast and also has the ability to preserve the active chemicals (alkaloids, non-alkaloids, electrolytes, minerals, etc.) in their natural form (as it does not involve heating and denaturation at any stage of the process). chlorofluorocarbon, being a highly volatile compound with its boiling point at $-21°$ C., evaporates fully after extraction yielding an ultrapure concentrate of the herbal ingredients.

After extraction, the concentrated extracts were recovered, filtered, and dried. The herbal ingredients were then mixed in the following proportions:

TABLE 2

Composition of capsule by weight.

| BOTANICAL NAME | PERCENT BY WEIGHT (%) OF THE COMPOSITION | mg/capsule |
|---|---|---|
| Glycine max | 13.3 | 100 |
| Plumbago zeylanica | 13.3 | 100 |
| Terminalia arjuna | 13.3 | 100 |
| Trigonella-foenum-graceumb | 13.3 | 100 |
| Coleus forskohlii | 13.3 | 100 |
| Commiphora mukul | 13.3 | 100 |
| Camellia sinensis | 13.3 | 100 |
| Azadirachta indica | 6.9 | 50 |

After premixing the ingredients in the specified quantities, the premix was blended in an automatic blender in order to prepare a homogeneous mixture. The blended and homogenized herbal mixture was filled in gelatin or vegetarian capsules in quantities of 750 milligrams each (to standardize the dosage to one capsule two or three times a day).

It will be appreciated by one of ordinary skill in the art that the amount of the herbal composition per capsule may vary depending on the individual, the condition being treated, or the frequency of dosage. It will further be understood by one of ordinary skill in the art that the herbal preparation according to the present invention can be administered in accordance with any conventional form of administration including, without limitation, a liquid or syrup, capsule, tablet, dairy beverage (such as a milk shake, protein drink, or a yogurt drink) or a snack bar.

Toxicity Tests

Acute toxicity—Fixed Dose Method: Acute toxicity was assessed in healthy adult female Sprague Dawley rats by administering a single oral dose of the present herbal preparation and observing the subjects for signs of toxicity over a fourteen (14) day period. The results of this acute toxicity study are useful to determine the doses for repeat dose toxicity studies and may also provide preliminary information on the target organ of toxicity.

In this study, the herbal preparation of the present invention was suspended in 0.1% aqueous carboxy methyl cellulose and administered by gavage route to rats using a ball-tipped intubation needle (18 G) and a syringe as per standard operating procedure (SOP) on Test Article/Substance (TA/S) administration Gavage/Intubation, (Sop No. IIT/S-PSC/16.2). Five (5) healthy female rats, acclimatized to laboratory conditions for seven (7) days prior to dosing, were used in this study. The rats were deprived of food for sixteen (16) hours before and three (3) hours after the administration of the test substance, but were given continuous access to water during this period. Observations of clinical signs were made at 10 minutes, 30 minutes, 60 minutes, 2 hours, 4 hours and 6 hours after dosing on day 1 and once per day thereafter for fourteen (14) days at approximately the same time each day. Observations of interest included changes in the subjects' skin, fur, eyes and mucous membrane, and monitoring of the subject's respiratory, circulatory, autonomic and central nervous system and somatomotor activity and behavioral pattern. Particular attention was directed to the observation of tremors, convulsion, salivation, diarrhea, lethargy, sleep and coma.

The sighting study did not reveal any signs of intoxication in a first rat treated at a dose level of 2000 mg/kg during the study period. Therefore, the main study was continued at the dose level of 2000 mg/kg body weight in the remaining four (4) rats. In the main study no signs of intoxication were observed in rats treated at the dose level of 2000 mg/kg. All subjects survived the fourteen (14) day study period. Gross pathological examination did not reveal any abnormalities in the test subjects. The herbal preparation of the present invention falls into Category 5 of the Globally Harmonized System (GHS) when administered orally in Sprague Dawley rats, Subacute toxicity: Subacute toxicity was studied by orally administering the present herbal composition to male and female Sprague Dawley rats on a daily basis for 28 days and observing the test subjects for an additional fifteen (15) days following administration of the composition before sacrificing them. The herbal formulation was suspended in 0.1% aqueous carboxy methyl cellulose vehicle and freshly prepared every day for the twenty-eight (28) day period. The control subjects were administered the vehicle only, without the herbal ingredients. The herbal preparation was administered to five (5) male and five (5) female rats at the dose levels 250 mg/kg, 500 mg/kg and 1000 mg/kg body weight. Two (2) additional dose levels were added to the study at 0 mg/kg (Reversal) and 1000 mg/kg (Reversal), in order to study the reversibility or delayed occurrence of symptoms, if any. The subjects were monitored for food consumption, body weight changes, signs of toxicity, sensomotor activity, and mortality. On the day of sacrifice, blood was collected for complete blood counts, urine and liver function tests. Organs were harvested for gross and microscopic examination.

There were no instances of mortality in any of the rats treated with the herbal formulation of the present invention in any of the treated dose groups up to 1000 mg/kg throughout the 28 day dosing period and the 14 day recovery period. No signs of intoxication were observed during this period. Male and female animals from all the treated dose groups showed similar levels food consumption and had comparable body weight gain to that of the control animals throughout the 28 day dosing period and the 14 day recovery period. Physical examination, gross and microscopic analysis of the organs, hematological analysis and biochemical tests in the blood and urine of the animals did not show any signs of toxicity up to 500 mg/day doses. In the case of the highest dose tested (1000 mg/day), there was a small increase in alkaline phosphatase in male and female animals sacrificed at the end of the dosing period ($29^{th}$ Day); however, these abnormalities were reversed in animals allowed to recover for an additional fifteen (15) days after the twenty-eight (28)-day dosing period (44th day). Similarly, there were significant increases in organ weight in the animals dosed at 1000 mg/day, but none were associated with histopathological abnormalities.

Based on these findings, the no observed effect level (NOEL) of the herbal composition of the present invention was found to be approximately 500 mg/kg body weight for male and female animals when orally administered in Sprague Dawley rats over a period of 28 days.

Ames test: A mutagenicity assay was performed using the Ames test to assess any mutagenic potential of the herbal formulation. *Salmonella* Reverse Mutation Assay was conducted using *Salmonella typhimurium* tester strains viz. TA97a, TA 98, TA 100, TA 1535 and TA 102. The mutagenic potential of this herbal medicine was tested at concentrations of 61.72, 185.18, 555.55, 1666.67 and 5000.00 µg/plate using dimethylsulfoxide (DMSO) as a vehicle. The study was conducted with and without metabolic activation (S9 fraction containing both cytosol and microsomes) prepared from sodium phenobarbital induced rat liver. The vehicle control and appropriate positive controls (methyl methane sulphonate, sodium azide, 4-nitroquinolene-N-oxide—for "without metabolic activation;" and 2-aminofluorene, 2-aminoanthracene and danthron—for "with metabolic activation") were tested simultaneously. Two (2) experiments were carried out using each tester strain with plating in triplicates at each concentration. The study showed that the mean number of revertant colonies counted at different concentrations were comparable to that of the controls for both the experiments, in the absence and presence of metabolic activation. The number of revertant colonies in the positive controls increased by 3.76 to 157.25 fold under identical conditions. This herbal medicine did not induce mutations in *Salmonella typhimurium* even at the highest concentration tested (5000.00 µg/plate), and, therefore, is not mutagenic in this *Salmonella* Reverse Mutation Assay.

Human Clinical Trials

Phase II Open Label Dose Comparison Study in Patients With Hyperlipidemia:

This study was conducted in accordance with International Conference on Harmonisation/Good Clinical Practice (ICH-GCP) guidelines. A total of 62 adults (age 30 and above) of either sex with moderate hyperlipidemia (total cholesterol>240 mg/dl and/or LDL-C>160 mg/dl) and no other major illnesses were enrolled in this 12-week open label, randomized multi-centric study with no concurrent lifestyle changes. The subjects were placed in two (2) groups and administered either 1500 mg (Group I) or 2250 mg (Group II) of the present herbal composition in accordance with the formulation set forth in Table 2 on a daily basis (i.e. 2 or 3 capsules). Subjects were randomized to either treatment groups in the order of their pre-determined randomization number. During the course of this study the patients were not allowed to take statin therapy, intake special diets or modify normal dietary habits or lifestyle that could potentially influence blood cholesterol levels in the body.

Patients were asked to grade the effect of the treatment and compared to that of the investigators' response. The grading for the Global Assessment of Therapy by both patient and investigator for relief of symptoms and no side effects as excellent, good, fair, poor and very poor.

Tests were done to assess the safety and efficacy of the present herbal composition. Safety parameters such as vitals (pulse rate/minute), blood pressure (mm of Hg), temperature (degree Celsius), respiratory rate (per minute)), systemic examination (central nervous system, cardiovascular system, respiratory system, gastrointestinal system, genitourinary system), complete blood count (CBC), erythrocyte sedimentation rate (ESR), serum glutamic pyruvic transaminase (SGPT), serum creatinine and urine routine were assessed at baseline and end of treatment. Total lipid profile (total cholesterol (TC), low density lipoprotein (LDL), very low density lipoprotein (VLDL), high density lipoprotein (HDL) and triglycerides (TG)), C-reactive protein (CRP), oxidized LDL, blood sugar level (BSL) and body mass index (BMI) were all measured in the blood at 4, 8 and 12 weeks. Efficacy of the present herbal composition was determined by biochemical analyses for the primary variable LDL-C and secondary variables VLDL-C, HDL-C, TG, TC, oxidized LDL and CRP.

Statistical significance for the demographics was assessed by Chi-square analysis. Significance for the biochemical parameters, LDL, oxidized LDL, VLDL, HDL, etc., before and after treatment were calculated using paired t-tests and using unpaired t-tests between Groups I and II. Changes in CRP was compared by using chi-square test ($p<0.05$ was considered significant). Statistical analyses were performed using SPSS 11.5, PEPI, INFO 2002 or Microsoft Excel software. The sample size required for the study was calculated to be 30 for each group (total of 60 for 2 groups) based on the primary variable LDL-C.

Of the 62 patients enrolled, 59 patients completed the study, one subject withdrew from the study and 2 subjects were dropped out for non-compliance. There was no significant difference in the demographics age (average of 48.93±9.35 vs. 46.50±7.95 years), gender and diet between Groups I and II. Although, there was a small but significant difference in the BMI (average of 26.95 vs. 29.22 kg/m2) between groups I and II, the vital parameters, such as pulse rate, blood pressure and respiratory rate showed only a small but insignificant difference throughout the length of the study. The average systolic blood pressure at week 8 and diastolic blood pressure at week 12 for Group 2 was significantly higher than Group 1. The laboratory safety parameters CBC, ESR, SGPT, and serum creatinine (data not shown) and the efficacy parameters LDL-C, VLDL-C and triglycerides, but not total cholesterol, showed a small but non-significant difference between the two groups at the baseline and week 12 (FIG. 1). There were no systemic abnormalities noted in patients in either group during the course of the study (data not shown). There were also no adverse and/or serious adverse events reported for either treatment group (data not shown). The herbal composition of the present invention was well-tolerated at both low and high doses. Further, there were no reports of any side effects like headache, nausea, vomiting, indigestion, constipation, diarrhea, rashes, or myalgia during the course of the 12-week study.

Figure 1B:
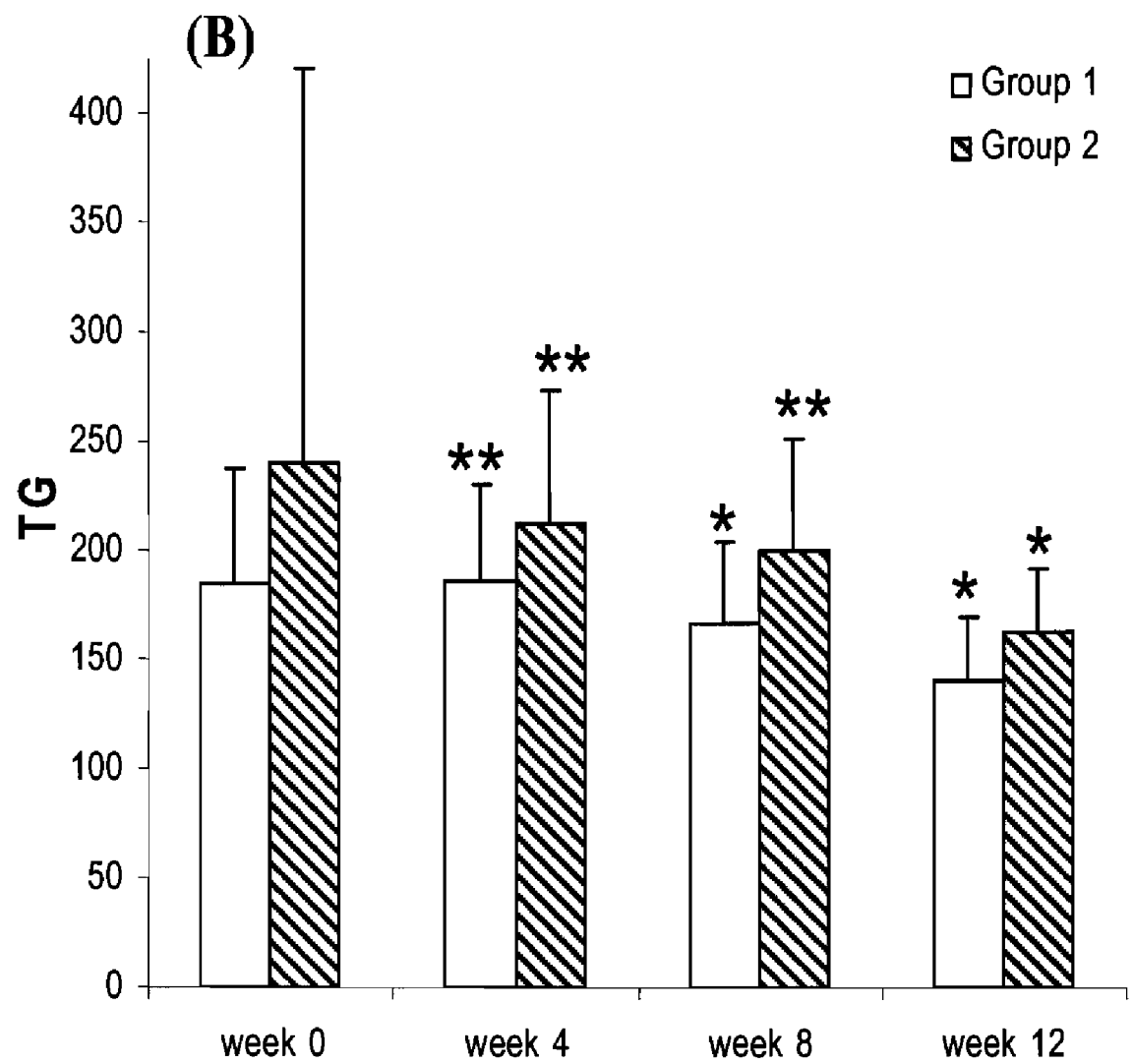
Figure 1C:
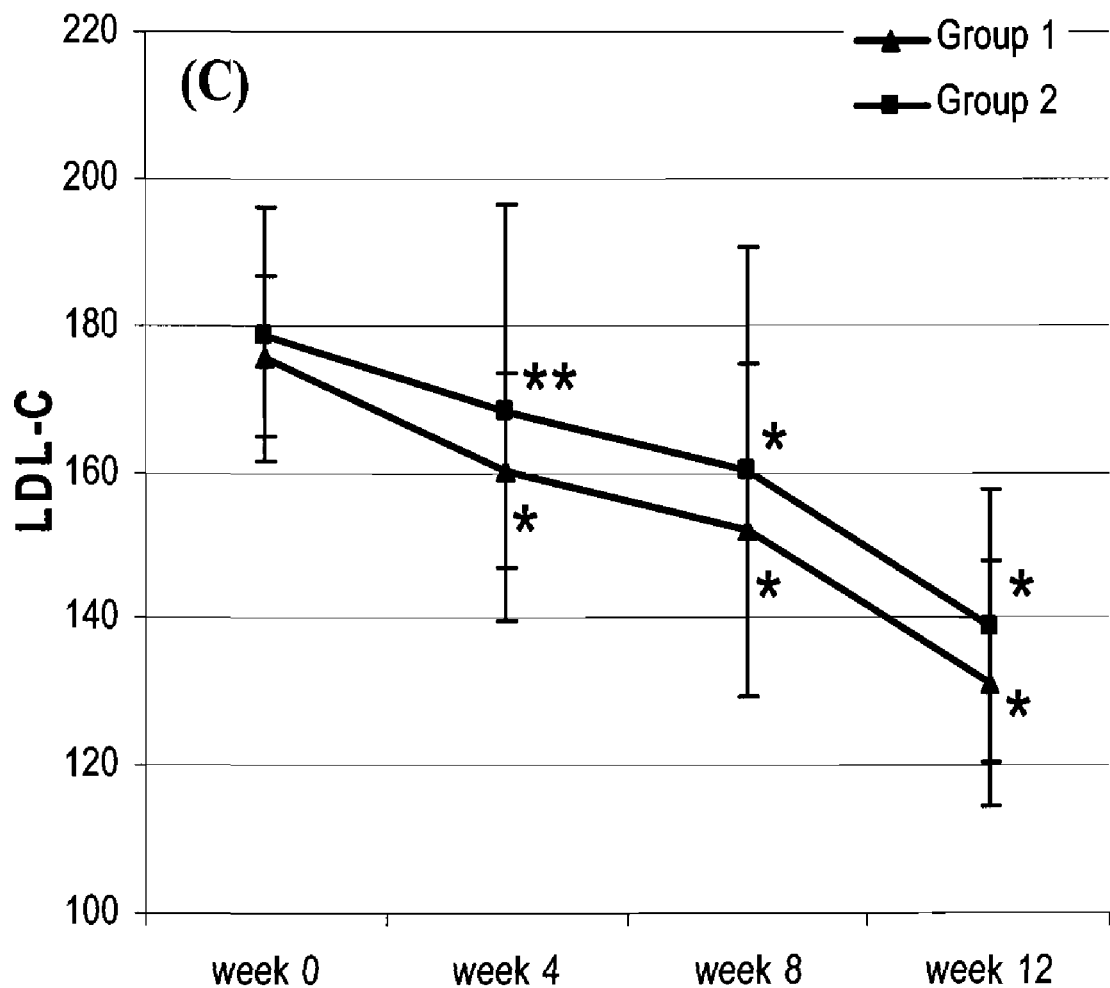
Figure 1D:
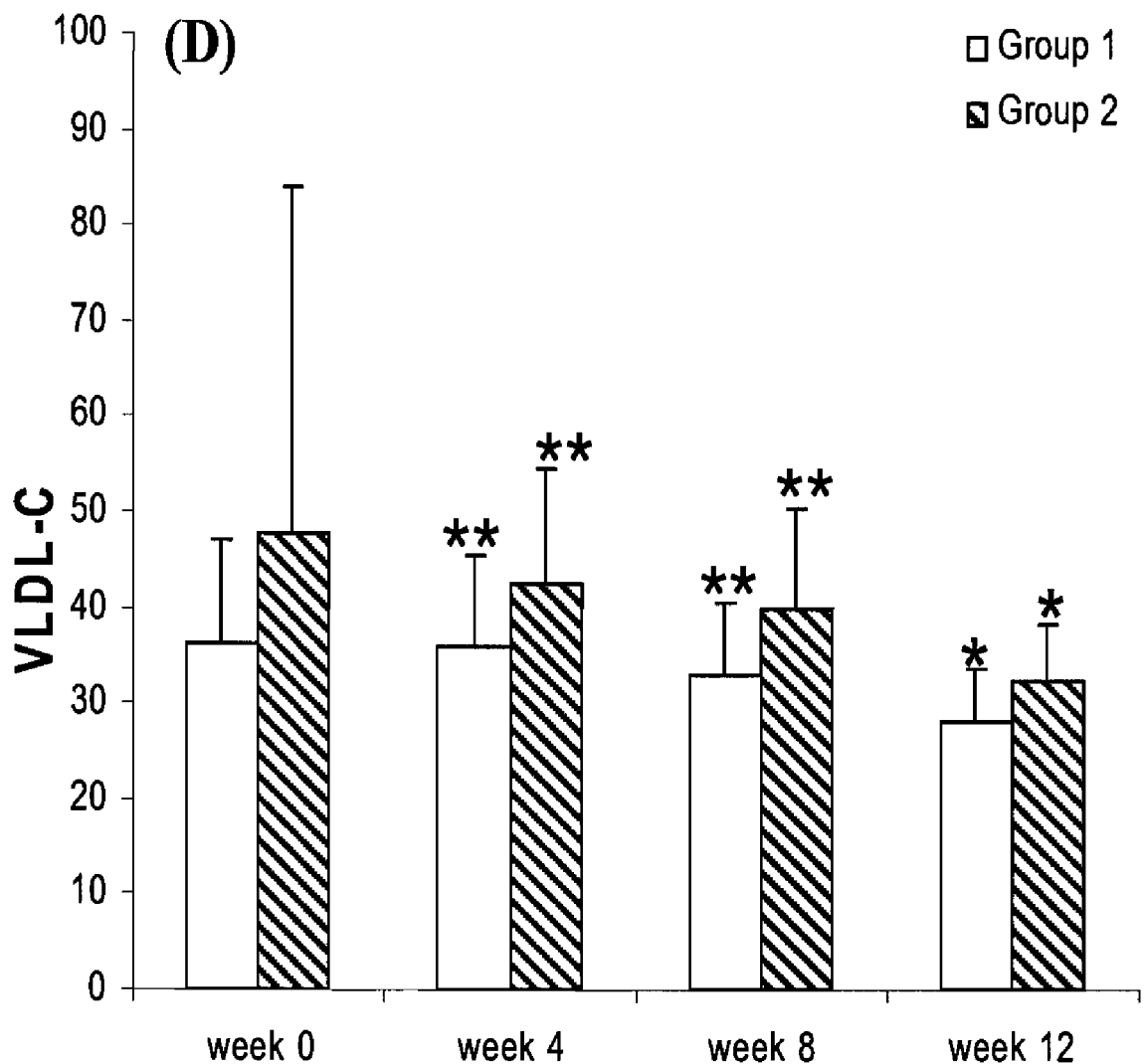

FIGS. 1(A) through 1(D) show the response of both Group's blood total cholesterol (TC) (FIG. 1(A)), total triglycerides (TG) (FIG. 1(B)), low density lipoprotein-cholesterol (LDL-C) (FIG. 1(C)), and very low density lipoprotein-cholesterol (VLDL-C) (FIG. 1(D)) during the twelve (12) week course of treatment with the present herbal composition. Results are presented as Mean±SD, wherein a p-value less than 0.05 ($p<0.05$) is identified as (*) and a p-value greater than 0.05 ($p>0.05$) is identified as (**) and considered not significant, compared to the baseline at week 0, using a paired t-test.

Following treatment with the herbal composition of the present invention, there was a significant lowering in total cholesterol, LDL-cholesterol, VLDL-cholesterol and triglyceride levels in the blood in both Groups I and II compared to the baseline (FIG. 1). However, the high-dose group (II) showed a more dramatic decrease throughout the twelve (12) week treatment. Furthermore, the decrease in VLDL-C (11.3%) and triglycerides (11.2%) was evident by four (4) weeks in the high dose group but not in the low dose group VLDL (−0.3%) and triglycerides (0.4%) suggesting that the high dose had both a faster effect and greater efficacy compared to the low dose group. However, HDL-C was not significantly different in either group after twelve (12) weeks of treatment. Oxidized LDL was not significantly different in the six (6) patients who were tested from Group II at the baseline and at week twelve (12).

There was a significant decrease in the blood CRP, an independent marker of cardiovascular risk, in both groups at 8 and 12 weeks compared to the baseline (Table 3). This decrease was acute in the high dose group. The response in the low dose group was slow but sustained.

TABLE 3

C-reactive Protein levels during the course of treatment.

| Parameter | | Group 1 | | | Group 2 | | |
|---|---|---|---|---|---|---|---|
| Number of Patients recruited | | 32 | | | 30 | | |
| Number of patients did CRP at Week 0 | | 24 | | | 25 | | |
| Number of patients with elevated CRP at Week 0 | | 10 | | | 9 | | |
| Number of patients repeated the test Week 8 and week 12 visits | | 6 | | | 7 | | |
| Week | Week 0 | Week 8 | Week 12 | Week 0 | Week 8 | Week 12 |
| Mean of CRP | | 7.40 | 7.14 | 4.87 | 11.11 | 4.75 | 8.99 |
| % Reduction in CRP | From Week 0 to Week 8 | | 3.55% | | | 57.24% | |
| | From Week 0 to Week 12 | | 34.17% | | | 19.04% | |

The precise mechanism of action of the present herbal composition is currently known. However, it is speculated that it is a result of a composite of the different effects brought about by the individual herbs in the present composition. Chief among them is the hypocholesterolemic property of several individual herbs in the present composition including guggul (*Commiphora mukul*), fenugreek (*Trigonella foenumgraecum*), neem (*Azadirachta indica*), soy (*Glycine max*), and arjuna (*Terminalia arjuna*). Guggul, and fenugreek, have been studied extensively and are associated with reductions in serum cholesterol ranging from 10% to 33% in randomized clinical studies in patients with different diagnoses. *Azadirachta indica* was shown to lower cholesterol and LDL-cholesterol in normal persons compared to placebos in a comparative study in subjects with and without malaria. Soy (*Glycine max*) has been shown to lower cholesterol by 10% in addition to being anti-atherogenic. Capsulated, purified sterols from soy in combination with other stannols and fatty acids have recently been shown to be an effective strategy to improve blood lipid profiles by altering lipoprotein ratios in hypercholesterolemic patients without any dietary intervention. Although the precise mechanism by which this decrease in cholesterol levels is brought about is currently unknown, one possible mechanism is through the action of phytosterols present in soy and several other plants that have been shown to inhibit cholesterol absorption in the small intestine. This results in lower serum cholesterol levels, possibly because of lower systemic availability. Isoflavones present in soy may also act through cyclic AMP signaling cascade to inhibit lipid biosynthesis.

Lipids are highly susceptible to free radical damage resulting in lipid peroxidation. Oxidized LDL plays an important role in the build of atherosclerotic plaques and the subsequent inflammation it triggers. The antioxidant properties of herbs are of particular interest in view of the impact of oxidative modification of LDL-C in the development of atherosclerosis. *A. indica*, *C. sinensis*, Ceylon leadwort (*Plumbago zeylanica*), *C. mukul*, and *T. foenum-graecum* have all been shown to have antioxidant effects. A recent study shows that *T. arjuna* protects the heart against oxidative injury in a ischemia-repurfusion through antioxidant enzymes and heat shock proteins in rabbits. Green tea (*Camellia sinensis*) also has a well documented antioxidant effect. It has been shown to lower oxidized LDL as well as soluble vascular cell adhesion molecule-1 (sVCAM-1), a marker for atherosclerosis and also to possess anti-thrombotic effects in vitro.

Mechanistic leads pointing to the efficacy of these herbs have mostly come from animal models. *T. arjuna* was shown to lower cholesterol and LDL levels over a 60 day period through inhibition of hepatic cholesterol synthesis, and bile acid secretion in diet-induced hyperlipidemic rabbits. *P. zeylanica* was shown to express antioxidant effects, decrease platelet adhesion, and cause regression of atheromatous plaque, and lower serum cholesterol and LDL in mice, rats, and hyperlipidemic rabbits. *A. indica* was shown to have cardio-tonic effects in rabbits and pigs, and at low doses has been shown to induce anxiolytic effects 45 min. after administration to rats. *Coleus* (*Coleus forskohlii*) was also shown to have cardio-tonic effects in dogs and cats. It is also possible that the ingredients in the present herbal compositions act through hormonal mediation. The cardioprotective effect of *T. arjuna* has been shown to be linked to its effect on thyroid function. It is also possible that soy can act through pytoestrogens to modulate hormonal systems.

*T. foenum-graecum* is also known to have hypoglycemic effects. Hyperglycemia is also a known risk factor for hyperlipidemia. It is tempting to speculate that this hypoglycemic effect of *T. foenum-graecum* present in the present herbal composition may also prove useful in diabetic persons. In this present study, however, there were no changes in the blood sugar level noted in either treatment group during the course of the study (FBS, 99.97±21.79 vs. 99.49±20.28 and PPBS, 128.97±48.51 vs. 135.22±59.6 for low dose group at weeks 0 and 12, respectively and FBS, 105.41±26.45 vs. 105.72±28.62 and PPBS, 130.79±44.29 vs. 131.31±41.57 for the high dose group at weeks 0 and 12, respectively). This observation is similar to the effect seen in experimental diabetes in rats where the effect of fenugreek was greater in diabetic rats compared to control non-diabetic rats since the subjects in our study were non-diabetic. Additional clinical studies in diabetic individuals need to be done with the present herbal composition because there is no literature available on the interaction of *T. foenum-graecum* with conventional hypoglycemic drugs, and the effect of the present herbal composition in these individuals taking anti-diabetic drugs is unknown.

It can seen from the results from the clinical study that the present herbal composition showed significant lipid-lowering effect in both male and female patients with moderate hyperlipidemia without any side effects or adverse events at both the doses tested. As can be seen from the data presented above, there was a significant lowering in blood total cholesterol, LDL-C, VLDL-C and triglyceride levels with no changes in the safety parameters after completion of therapy with the present herbal composition for 12 weeks. HDL-C and oxidized LDL showed small non-significant changes at week 12 compared to baseline in both the groups. Triglycerides and VLDL decreased by about 32% and LDL and Total Cholesterol decreased by about 23-25% in the high dose group compared to ~20-25% overall changes in the low dose group by week 12. The level of CRP decreased significantly in both groups at weeks 8 and 12 compared to baseline (34.2% vs. 19.1% at week 12) with the high dose group again showing a more acute response than the low dose group (57.2% vs. 3.5% week 8).

The high dose group had a more rapid onset (week 4) and greater efficacy. The present herbal composition also caused a decrease in CRP levels suggesting that in addition to reversing moderate hypelipidemia, it can also delay the progression and/or onset of myocardial infarction in patients at high risk for the disease.

It will be appreciated by those of ordinary skill in the art that changes could be made to the embodiments made above without departing from the broad inventive concept thereof. It can be understood, therefore, that this invention is not limited to the particular embodiments disclosed, but is intended to cover modifications within the spirit and scope of the present invention as defined by the appended claims.

What is claimed is:

1. A pharmaceutical composition for treating hyperlipidemia, the composition comprising:
    Glycine max seed extract in an amount of 10-15% by weight of the composition, wherein the Glycine max seed extract contains about 40% isoflavones;
    Plumago zeylanica root extract in an amount of 10-15% by weight of the composition, wherein the Plumago zeylanica root extract contains about 0.08-0.15% alkaloids;
    Terminalia arjuna bark extract in an amount of 10-15% by weight of the composition, wherein the Terminalia arjuna bark extract contains about 25% tannins and greater than 1% arjunic acid;
    Trigonella-foenum graceum seed extract in an amount of 10-15% by weight of the composition, wherein the Trigonella-foenum graceum seed extract contains about 10% saponins;
    Coleus forskohlii root extract in an amount of 10-15% by weight of the composition, wherein the Coleus forskohlii root extract contains greater than 2.5% forskolin;
    Commiphora mukul resin extract in an amount of 10-15% by weight of the composition, wherein the Commiphora mukul resin extract contains about 2.5-10% guggal sterones;
    Camellia sinensis leaf extract in an amount of 10-15% by weight of the composition, wherein the Camellia sinensis leaf extract contains greater than 45% polyphenols; and
    Azadiracta indica bark extract in an amount of 5-7.5% by weight of the composition, wherein the Azadiracta indica bark extract contains about 2.5% bitters.

2. The composition of claim 1 wherein the composition comprises:
    said Glycine max in an amount of 13.3% by weight of the composition;
    said Plumago zeylanica in an amount of 13.3% by weight of the composition;
    said Plumago zeylanica in an amount of 13.3% by weight of the composition;
    said Trigonella-foenum graceum in an amount of 13.3% by weight of the composition;
    said Coleus forskohlii in an amount of 13.3% by weight of the composition;
    said Commiphora mukul in an amount of 13.3% by weight of the composition;
    Camellia sinensis in an amount of 13.3% by weight of the composition; and
    said Azadiracta indica in an amount of 6.9% by weight of the composition.

3. The composition of claim 1, wherein the composition is administered in at least one form selected from the group consisting of: a gelatin capsule, a vegetarian capsule, a tablet, a liquid, a syrup, a dairy beverage, and a snack bar.

4. A method of treating hyperlipidemia in a person in need thereof, comprising administering to the person a composition comprising:
    Glycine max seed extract in an amount of 10-15% by weight of the composition, wherein the Glycine max seed extract contains about 40% isoflavones;
    Plumago zeylanica root extract in an amount of 10-15% by weight of the composition, wherein the Plumago zeylanica root extract contains about 0.08-0.15% alkaloids;
    Terminalia arjuna bark extract in an amount of 10-15% by weight of the composition, wherein the Terminalia arjuna bark extract contains about 25% tannins and greater than 1% arjunic acid;
    Trigonella-foenum graceum seed extract in an amount of 10-15% by weight of the composition, wherein the Trigonella-foenum graceum seed extract contains about 10% saponins;
    Coleus forskohlii root extract in an amount of 10-15% by weight of the composition, wherein the Coleus forskohlii root extract contains greater than 2.5% forskolin;
    Commiphora mukul resin extract in an amount of 10-15% by weight of the composition, wherein the Commiphora mukul resin extract contains about 2.5-10% guggal sterones;
    Camellia sinensis leaf extract in an amount of 10-15% by weight of the composition, wherein the Camellia sinensis leaf extract contains greater than 45% polyphenols; and
    Azadiracta indica bark extract in an amount of 5-7.5% by weight of the composition, wherein the Azadiracta indica bark extract contains about 2.5% bitters; and
    wherein the composition is administered in at least one form selected from the group consisting of: a gelatin capsule, a vegetarian capsule, a tablet, a liquid, a syrup, a diary beverage and a snack bar.

* * * * *

UNITED STATES PATENT AND TRADEMARK OFFICE
CERTIFICATE OF CORRECTION

PATENT NO. : 8,067,043 B2  Page 1 of 1
APPLICATION NO. : 12/188566
DATED : November 29, 2011
INVENTOR(S) : Nandkishor Bapurao Managoli It is certified that error appears in the above-identified patent and that said Letters Patent is hereby corrected as shown below:

In the Claims:

In claim 2, at column 12, line 3, delete "*Plumago zeylanica*" and insert therefor --*Terminalia arjuna*--.

In claim 2, at column 12, line 11, delete "Camellia sinensis" and insert therefor --said *Camellia sinensis*--.

Signed and Sealed this
Fourth Day of June, 2013

Teresa Stanek Rea
*Acting Director of the United States Patent and Trademark Office*